United States Patent
Spohn et al.

(10) Patent No.: US 10,403,010 B2
(45) Date of Patent: Sep. 3, 2019

(54) METHODS AND SYSTEMS FOR RECONSTRUCTING IMAGES

(71) Applicant: General Electric Company, Schenectady, NY (US)

(72) Inventors: Michael Lee Spohn, Waukesha, WI (US); Robert Johnsen, Pewaukee, WI (US); Kenneth Vosniak, Wauwatosa, WI (US); Kathryn Littlejohn, Wales, WI (US)

(73) Assignee: General Electric Company, Schenectady, NY (US)

( * ) Notice: Subject to any disclaimer, the term of this patent is extended or adjusted under 35 U.S.C. 154(b) by 52 days.

(21) Appl. No.: 15/709,160

(22) Filed: Sep. 19, 2017

(65) Prior Publication Data

US 2019/0087986 A1    Mar. 21, 2019

(51) Int. Cl.
| | |
|---|---|
| *G06T 11/00* | (2006.01) |
| *G16H 30/00* | (2018.01) |
| *A61B 6/03* | (2006.01) |
| *A61B 5/055* | (2006.01) |

(52) U.S. Cl.
CPC .......... *G06T 11/008* (2013.01); *G06T 11/005* (2013.01); *G16H 30/00* (2018.01); *A61B 5/055* (2013.01); *A61B 6/03* (2013.01)

(58) Field of Classification Search
CPC ..... G06T 11/008; G06T 11/005; G16H 30/00; A61B 5/055; A61B 6/03
USPC .......................................................... 382/131
See application file for complete search history.

(56) References Cited

U.S. PATENT DOCUMENTS

| | | | |
|---|---|---|---|
| 5,031,089 A | 7/1991 | Liu et al. | |
| 7,381,959 B2 | 6/2008 | Manjeshwar et al. | |
| 9,111,059 B2 | 8/2015 | Pattichis et al. | |
| 9,542,198 B2 | 1/2017 | Pattichis et al. | |
| 2006/0145082 A1 | 7/2006 | Stearns et al. | |
| 2010/0152577 A1* | 6/2010 | Young | A61B 6/5247 600/431 |
| 2013/0204113 A1* | 8/2013 | Carmi | A61B 6/032 600/407 |

(Continued)

FOREIGN PATENT DOCUMENTS

CN    108109182    *   1/2018   ............ A61B 6/037

OTHER PUBLICATIONS

"Vue Point HD: Bringing accuracy to PET reconstruction," GE Healthcare Whitepaper, Available Online at http://www3.gehealthcare.co.uk/~/media/downloads/uk/education/pet%20white%20papers/mi_emea_vue_point_hd_white_paper_pdf_2009-07_doc0558367.pdf?Parent=%7BB66C9E27-1C45-4F6B-BE27-D2351D449B19%7D, Available as Early as Jun. 1, 2009, 8 pages.

(Continued)

*Primary Examiner* — Jerome Grant, II
(74) *Attorney, Agent, or Firm* — McCoy Russell LLP

(57) ABSTRACT

Methods and systems are provided for medical imaging systems. In one embodiment, a method includes receiving one or more image reconstruction parameters defining an image reconstruction process for reconstructing one or more images from medical imaging data, identifying a target hardware allocation based on the one or more image reconstruction parameters, and reconstructing, via computing device hardware as specified by the target hardware allocation, one or more images from the medical imaging data according to the image reconstruction process.

18 Claims, 4 Drawing Sheets

(56) References Cited

U.S. PATENT DOCUMENTS

| | | | | |
|---|---|---|---|---|
| 2014/0003689 A1* | 1/2014 | Asma | | G06T 11/006 |
| | | | | 382/131 |
| 2014/0056500 A1* | 2/2014 | Bal | | G06T 11/005 |
| | | | | 382/131 |
| 2014/0140602 A1* | 5/2014 | Aspelmeier | | G06T 11/006 |
| | | | | 382/131 |
| 2015/0119694 A1* | 4/2015 | Mihlin | | A61B 6/5205 |
| | | | | 600/411 |
| 2015/0213630 A1* | 7/2015 | Szirmay-Kalos | | G06T 11/006 |
| | | | | 382/131 |
| 2015/0230762 A1* | 8/2015 | Alpert | | A61B 6/037 |
| | | | | 600/425 |
| 2016/0020952 A1* | 1/2016 | Berke | | H04L 12/40 |
| | | | | 370/252 |
| 2016/0131774 A1* | 5/2016 | Lage | | A61B 6/481 |
| | | | | 600/426 |
| 2016/0161578 A1* | 6/2016 | Weissler | | G01T 1/1603 |
| | | | | 324/309 |
| 2016/0209523 A1* | 7/2016 | Moskal | | G01T 1/2985 |
| 2016/0266261 A1* | 9/2016 | Douglas | | G01T 1/2985 |
| 2017/0084025 A1* | 3/2017 | Lyu | | G06T 7/0012 |
| 2018/0114346 A1* | 4/2018 | Sun | | G01S 7/4866 |
| 2018/0144513 A1* | 5/2018 | Liu | | A61B 6/037 |
| 2018/0174360 A1* | 6/2018 | Feng | | G06T 17/20 |
| 2018/0315225 A1* | 11/2018 | Zhang | | G06T 5/00 |
| 2018/0350078 A1* | 12/2018 | Sun | | G06T 7/11 |
| 2018/0353147 A1* | 12/2018 | Wang | | A61B 6/037 |

OTHER PUBLICATIONS

Kapusta, P. et al., "Applying Parallel and Distributed Computing for Image Reconstruction in 3D Electrical Capacitance Tomography," Automatyka, vol. 14, No. 3/2, Available as Early as Jan. 1, 2010, 12 pages.

Bicer, T. et al., "Optimization of tomographic reconstruction workflows on geographically distributed resources," Journal of Synchrotron Radiation, vol. 23, No. 4, Jul. 1, 2016, 9 pages.

* cited by examiner

METHODS AND SYSTEMS FOR RECONSTRUCTING IMAGES

FIELD

Embodiments of the subject matter disclosed herein relate to non-invasive diagnostic imaging, and more particularly, to image reconstruction from medical imaging data.

BACKGROUND

Medical imaging creates visual representations of the interior of a body for medical diagnostics, physiology, research, and other functions. Medical imaging allows clinicians to visualize internal structures hidden by the skin and bones, as well as to diagnose and treat disease. Many different medical imaging modalities are currently available, including radiology, which uses the imaging technologies of X-ray radiography, magnetic resonance imaging, medical ultrasonography or ultrasound, and nuclear medicine functional imaging techniques such as positron emission tomography (PET) and single-photon emission computed tomography (SPECT).

Medical imaging scans may be performed according to a variety of scanning protocols, which may be dependent on the anatomy being scanned (e.g., cardiac versus oncologic), diagnostic goal of the scan, or other parameters. The different protocols may include different numbers of images and different image reconstruction protocols, for example.

BRIEF DESCRIPTION

In one embodiment, a method includes receiving one or more image reconstruction parameters defining an image reconstruction process for reconstructing one or more images from medical imaging data, identifying a target hardware allocation based on the one or more image reconstruction parameters, and reconstructing, via computing device hardware as specified by the target hardware allocation, one or more images from the medical imaging data according to the image reconstruction process.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of medical imaging systems. Medical imaging may be performed according to a variety of protocols and workflows, which results in variability in the time it may take to generate images for review. The variety of workflows prevents a single hardware allocation solution that optimizes image generation across sites or even across different workflows at the same site. Thus, methods and systems are provided herein for an automated and adaptable solution to optimize medical image reconstruction workflows to speed up the image reconstruction process and optimally utilize available hardware. In particular, the parameters defining the image reconstruction process, including the number of image reconstruction jobs (e.g., the number of images to be reconstructed), image reconstruction method, desired image resolution, size of the medical imaging data set, and so forth, may be used to predict how long the total image reconstruction process will take using a variety of different hardware resource configurations. For example, the duration of the total image reconstruction process may be calculated for a first configuration that includes reconstructing each image serially across all available hardware resources, for a second configuration that includes reconstructing two images in parallel, for a third configuration that includes reconstructing four images in parallel, etc. The configuration that provides the shortest duration may be selected and the images may be reconstructed using the selected configuration. In doing so, the overall reconstruction impact on an imaging workflow may be reduced, allowing clinicians to send images off for review earlier and potentially increasing throughput at the site by automatically optimizing the setup on a per-clinician and per-workflow basis.

Figure 1:
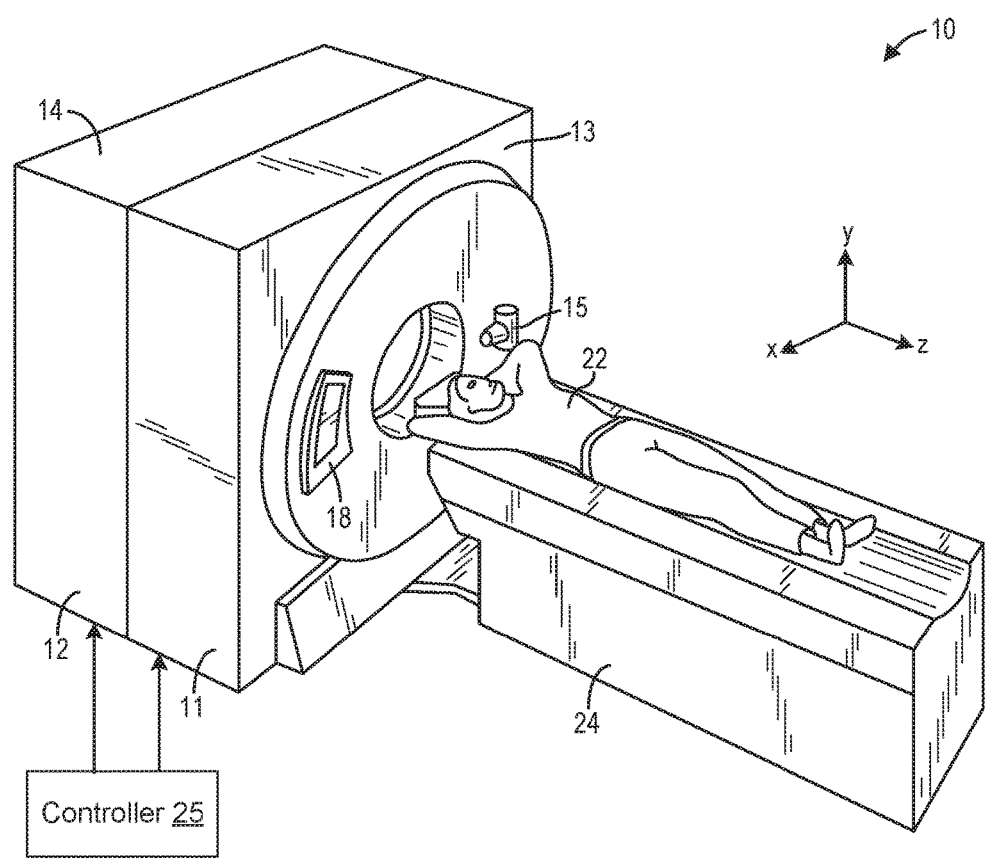
FIG. 1 shows a pictorial view of a multi-modality imaging system according to an embodiment of the invention.
Figure 2:
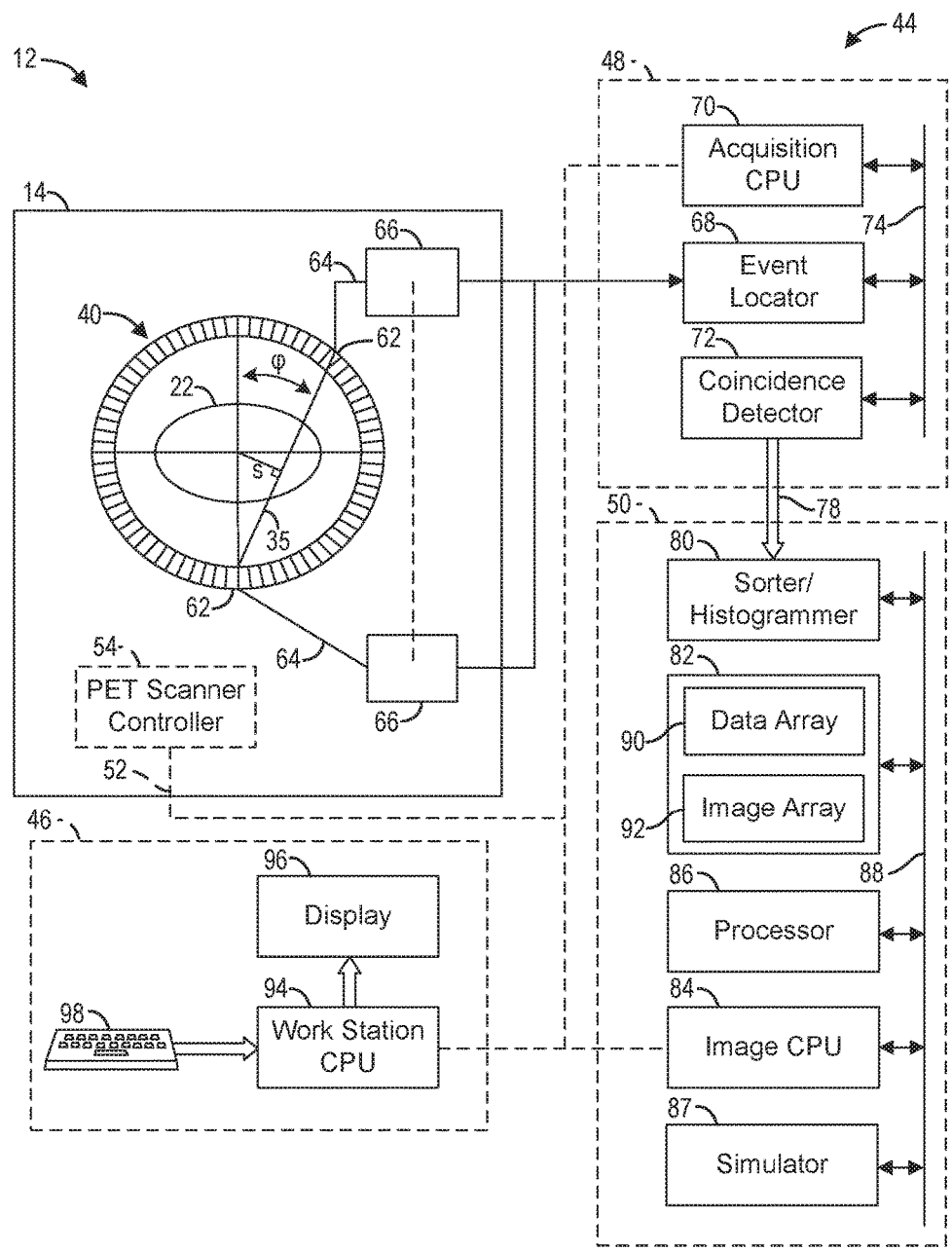
FIG. 2 shows a block schematic diagram of a positron emission tomography (PET) imaging system according to an embodiment of the invention.

An example of an imaging system that may be used to acquire images processed in accordance with the present techniques is provided in FIG. 1. Herein, the imaging system may be a multi-modality system. In one embodiment, the multi-modality imaging system may be a Computed Tomography/Positron Emission Tomography (CT/PET) imaging system wherein a first modality is a CT imaging system and a second modality is a PET imaging system (as illustrated in FIGS. 1 and 2, for example). Hardware resources of the imaging system (or operably coupled to the imaging system) may be used to reconstruct images from imaging information acquired by the imaging system, according to the hardware allocation process shown in FIG. 3 and the flow chart of FIG. 4, for example.

Though a CT/PET imaging system is described by way of example, it should be understood that the present techniques may also be useful when applied to images acquired using other imaging modalities, such as solely PET, solely CT, tomosynthesis, MRI, ultrasound, and so forth. The present discussion of a CT/PET imaging modality is provided merely as an example of one suitable imaging modality. In other examples, the hardware allocation based on scanning workflow may be performed with image data obtained using MRI, ultrasound, or other imaging modalities.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Various embodiments of the invention provide a multi-modality imaging system 10 as shown in FIGS. 1 and 2. Multi-modality imaging system 10 may be a suitable type of imaging system, for example, such as a Positron Emission Tomography (PET), a Single Photon Emission Computed Tomography (SPECT), a Computed Tomography (CT), an ultrasound system, Magnetic Resonance Imaging (MRI), or any other system capable of generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring to FIG. 1, the multi-modality imaging system 10 includes a first modality unit 11 and a second modality unit 12. The two modality units enable the multi-modality imaging system 10 to scan an object or patient in a first modality using the first modality unit 11 and in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g., the first modality 11 is a CT imaging system 11 and the second modality 12 is a PET imaging system 12. The CT/PET system 10 is shown as including a gantry 13 associated with a CT imaging system and a gantry 14 that is associated with a PET imaging system. For example, the CT imaging system may generate anatomical images of a patient, while the PET system may generate functional images corresponding to dynamic occurrences such as metabolism. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

In certain embodiments, the multi-modality imaging system 10 may include a common controller or processor 25 configured to operate both the CT imaging system 11 and the PET imaging system 12. In other embodiments, the CT and the PET imaging systems may each include a dedicated controller that separately controls the CT and the PET imaging systems.

FIG. 2 is a block schematic diagram of the PET imaging system 12 illustrated in FIG. 1 in accordance with an embodiment of the present invention. As described in detail below, PET generates images that represent the distribution of positron-emitting nuclides within the body of a patient. When a positron interacts with an electron by annihilation, the entire mass of a positron-electron pair is converted into two 511-keV photons (also referred to as 511-keV events). The photons are emitted in opposite directions along a line of response (LOR). The annihilation photons are detected by detectors that are placed on both sides of the LOR, in a configuration such as a detector ring. The detectors convert the incident photons into useful electrical signals that can be used for image formation. An image thus generated based on the acquired image data includes the annihilation photon detection information.

The PET imaging system 12 includes a detector ring assembly 40 including a plurality of detector crystals. The PET imaging system 12 also includes a controller or processor 44, to control normalization and image reconstruction processes. Controller 44 is coupled to an operator workstation 46. In one non-limiting example, the controller 44 may be an example of the controller 25 of FIG. 1. Controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22, may be positioned using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through the communication link 52. Therefore, the scanning operation is controlled from the operator workstation 46 through PET scanner controller 54.

During operation, when a photon collides with a crystal 62 on a detector ring 60, it produces a scintillation on the crystal. Each photomultiplier tube produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other, to indicate coincidence. Second, the line-of-response (LOR) formed by a straight line joining the two detectors that detect the coincidence event should pass through the field of view in the PET imaging system 12. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of image array 92. Resulting image arrays 92 are then stored in memory module 82.

Array processor 86 may comprise a single processor including one or more processing cores. In other examples, array processor 86 may include multiple processors, such as one or more CPUs and one or more graphics processing units (GPUs). In still further examples, array processor 86 may comprise multiple processors distributed across multiple devices, e.g., two CPUs and one GPU on a first device and two CPUs and one GPU on another device. Other processor configurations are possible.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system 12 and the positioning of the patient 22 for a scan. Similarly, the operator can control the display of the resulting image on the display 96 and can perform image-enhancement functions using programs executed by the workstation CPU 94. Further, user input information, for example selection of a PET scanning workflow protocol, may be communicated to array processor 86 in order to determine a target hardware allocation for carrying out an image reconstruction process, as described in more detail below.

Further, some PET detection methods may include Time-Of-Flight PET (TOF PET), where, in addition to coincidence detection, the difference in the detection time of the individual photons in the coincidence pair is measured. In TOF PET, upon detection of a radiation event (e.g., a gamma photon), the scintillator block at the detection locale time-stamps the detected radiation event. Since both the photons travel at the speed of light, the difference in their time stamps can be used to better localize the annihilation event along the LOR. Incorporation of the time of flight information helps localize the actual emission point for each event, thereby reducing statistical uncertainty in the reconstructed images.

Thus, as described above, array processor 86 receives a data array indicative of all events occurring along each projection ray and reconstructs images from the data array. The data collected by a PET scanner (e.g., sinogram data) is not an image that illustrates the spatial distribution of the radiotracer inside the patient. Certain mathematical operations are performed on the sinogram data to transform the data into images. The process of generating images is called "tomographic image reconstruction." The image reconstruction techniques are based on the fact that, when a coincidence event is detected by two detectors, the emission point must have occurred somewhere along the line (i.e., LOR) joining the two detectors. Various techniques may be used for tomographic image reconstruction. The techniques range from analytical methods which are computationally efficient to iterative reconstruction techniques which can be computationally demanding.

Two types of image reconstruction algorithms include analytical image reconstruction (e.g., confidence-weighted filtered back projection) and iterative reconstruction (e.g., confidence-weighted maximum-likelihood expectation maximization). Both of these algorithms for image reconstruction are based on the operation of back-projection, which converts the counts detected by a detector pair/time bin combination back into the image space. This is performed by smearing the counts (in appropriate proportions) at the appropriate location (as determined by the time bin) along the line joining the two detector elements.

Two iterative reconstruction algorithms used in PET image reconstruction are maximum likelihood expectation maximization (MLEM) and ordered subsets expectation maximization (OSEM). These iterative reconstructions may include iteration steps of: (a) transforming an estimate of the reconstructed image into an estimated sinogram, (b) adding the estimate of the scatter and random coincidences, (c) comparing the estimated sinogram with the measured prompts sinogram to generate a correction sinogram, (d) generating a correction to the estimated image by back-projecting the correction sinogram, and (e) updating the estimated image based on the correction. It should be noted that any reconstruction algorithms may be used other the ones described herein, modified as desired or needed.

Image reconstruction may be computationally intensive and different image reconstruction processes may have differing processing needs. For example, different image reconstruction methods (e.g., filtered back projection versus iterative reconstruction) may demand more or less parallel processing and more or less serial processing. Further, different image reconstruction processes may include varying numbers of iterations per image reconstruction, for example a user may desire more iterations to increase numerical accuracy. Further still, corrections may be applied for each image reconstruction, in order to reduce noise stemming from scatter and random coincidences, and these corrections may have varying processing needs. Also, depending on the anatomy being scanned, diagnostic goal of the scan, and other parameters, the number of images to be reconstructed may vary. As a result, some image reconstruction processes may be faster than other image reconstruction processes due to the varying parameters of each image reconstruction process that result in different processing needs.

Also as mentioned above, the array processor may include more than one processing unit, e.g., multiple CPUs and multiple GPUs, each having one or more processing cores. To expedite the image reconstruction process, the images may be reconstructed using more than one hardware unit, such as distributing the image reconstruction process across the CPUs and/or GPUs. However, as each image reconstruction job may have differing processing needs, a single fixed allocation of hardware resources may not provide the fastest image reconstruction possible for each image reconstruction job. For example, a first image reconstruction job may include a relatively higher amount of parallel processing and relatively lower amount of serial processing that may be performed faster using more GPU resources, while a second image reconstruction job may include a relatively lower amount of parallel processing and a relatively higher amount of serial processing that may be performed faster using more CPU resources.

As used herein, an image reconstruction process may include one or more image reconstruction jobs, where each image reconstruction job includes the image reconstruction processor reconstructing an image from a set of medical imaging data (such as PET data as described herein) collected during a scanning session performed on a subject (also referred to herein as an exam). An image reconstruction job may be defined by a set of medical imaging data (such as the data array 90) and reconstruction parameters that are received/obtained by the reconstruction processor, where the reconstruction parameters define how the image is to be reconstructed. The image reconstruction job may include one image that is to be reconstructed from the imaging data. An imaging reconstruction process may include all image reconstruction jobs for a given data set during a single exam/scanning session.

As described above, each image reconstruction job may be defined by various reconstruction parameters, such as reconstruction method, number/type of corrections applied, matrix size, and image resolution. In one example, these reconstruction parameters may define the types and number of processing tasks that need to be performed in order to reconstruct the image. For a given set of processing tasks associated with an image reconstruction job, the processing tasks may be defined at least in part according to whether the tasks are able to be performed in parallel or in series, how much processing power each task requires, and so forth.

According to embodiments disclosed herein, in order to expedite image reconstruction for multiple image reconstruction jobs, a simulator 87 may be provided (e.g., as part of the image reconstruction processor 50) that determines an optimal hardware resource allocation configuration for an image reconstruction process that may include more than one image reconstruction job. The simulator 87 may query hardware availability and identify a configuration/distribution of processing tasks defining the image reconstruction process across the available hardware. For example, the simulator may determine each hardware resource that is available at the time that the image reconstruction process is requested. This may include determining which resources of each processor are available (e.g., where an available resource includes the resource not currently being utilized to execute other programs, such as an operating system), such as determining which or how many Arithmetic Logic Units (ALUs) of each processing unit are available to perform image reconstruction.

The simulator may identify, for the image reconstruction process, a shortest "time to final image" duration, e.g., the shortest amount of time for completion of the image reconstruction process using the available hardware. To accomplish this, the simulator may determine a plurality of possible "time to final image" durations for the image reconstruction process, with each possible duration calculated using a different hardware resource allocation configuration. In one example, the different possible hardware allocation configurations may be defined by allocating processing tasks into processing queues, such that different image reconstruction processes may include different numbers of processing queues, such as one queue, two queues, four queues, etc. For a configuration that includes one queue, each processing task associated with an image reconstruction process may be performed serially using all available hardware resources. For a configuration that includes two queues, two processing tasks associated with an image reconstruction process may be performed in parallel across the available hardware resources. For a configuration that includes four queues, four processing tasks associated with an image reconstruction process may be performed in parallel across the available hardware resources.

However, other mechanisms for allocating the processing tasks to the available hardware resources are possible, such as defining the processing tasks and allocation into queues by image. For example, in a first configuration that includes one image processing queue, image reconstruction may be performed serially across all available resources by image, such that one image is reconstructed using all available processing resources, followed by another image. In a second configuration that includes two or more image processing queues, image reconstruction may be performed in parallel across the available hardware resources, such that two (or more) images may be reconstructed in parallel (e.g., simultaneously/at the same time using different subsets of the available processing resources).

In one example, the simulator may access information stored in memory that identifies predicted reconstruction durations for a plurality of image reconstruction jobs and hardware configurations. For example, a table stored in memory may include a plurality of image reconstruction jobs that are defined by various reconstruction parameters, such as reconstruction method, number/type of corrections applied, matrix size, and image resolution. Each image reconstruction job listed in the table may be associated with a plurality of durations where each respective duration is for a single iteration of the reconstruction job using a given possible hardware configuration. Then, based on the number of iterations requested by the user, a total duration for the image reconstruction job, for a given hardware allocation, may be determined. The simulator may identify the shortest time to last image for an image reconstruction process and dynamically reconfigure the hardware allocation appropriately.

As an example, a given image reconstruction process may include four processing tasks, as defined by the image reconstruction parameters (e.g., reconstruction method, matrix size, and resolution). The simulator may determine that performing each task using all the available resources may take 30 seconds per task, resulting in total iteration time of 120 seconds. The simulator may determine that performing each task using half the available resources may take 50 seconds per task. However, because only half the resources are used per task, two tasks may be performed at the same time, resulting in a total iteration time of 100 seconds. Thus, while the per-task time may be higher using half the available resources, the total time may be lower.

The various image reconstruction parameters described above (such as iterations, corrections, or the matrix size) each impact the image reconstruction process duration. For example, an increased number of iterations, an increased number of corrections, and an increased matrix size each increase the reconstruction time. Using less hardware for a given image reconstruction job also increases the reconstruction duration. However, the increase in duration as a result of reducing the hardware the reconstruction is performed on may not be a one-to-one correlation with the reduction in hardware. For example, reducing the hardware by 50% does not necessarily result in a reconstruction duration that is twice as long for a given reconstruction job. Thus, while splitting up the hardware may make individual jobs slower, the overall process may be faster so long as all the hardware is being used a sufficiently high percentage of the time.

In some examples, the different hardware configurations may allow for allocation of processing tasks to specific hardware. For example, a first processing task (which may include a first image reconstruction job in one example) may be allocated to be performed by a CPU, while a second processing task may be allocated to be performed by a GPU. Additionally or alternatively, when hardware resources are distributed across more than one physical device, the additional time for transmission/reception of information among the physical devices may be included as part of the image reconstruction duration information. For example, a given image reconstruction job may be determined to be performed faster if the reconstruction job is performed using multiple processing units rather than a single processing unit. However, if those multiple processing units are located on separate devices, the transit time for sending/receiving the image processing information may result in a longer reconstruction duration than simply performing the reconstruction job on a single processing unit.

Figure 3:
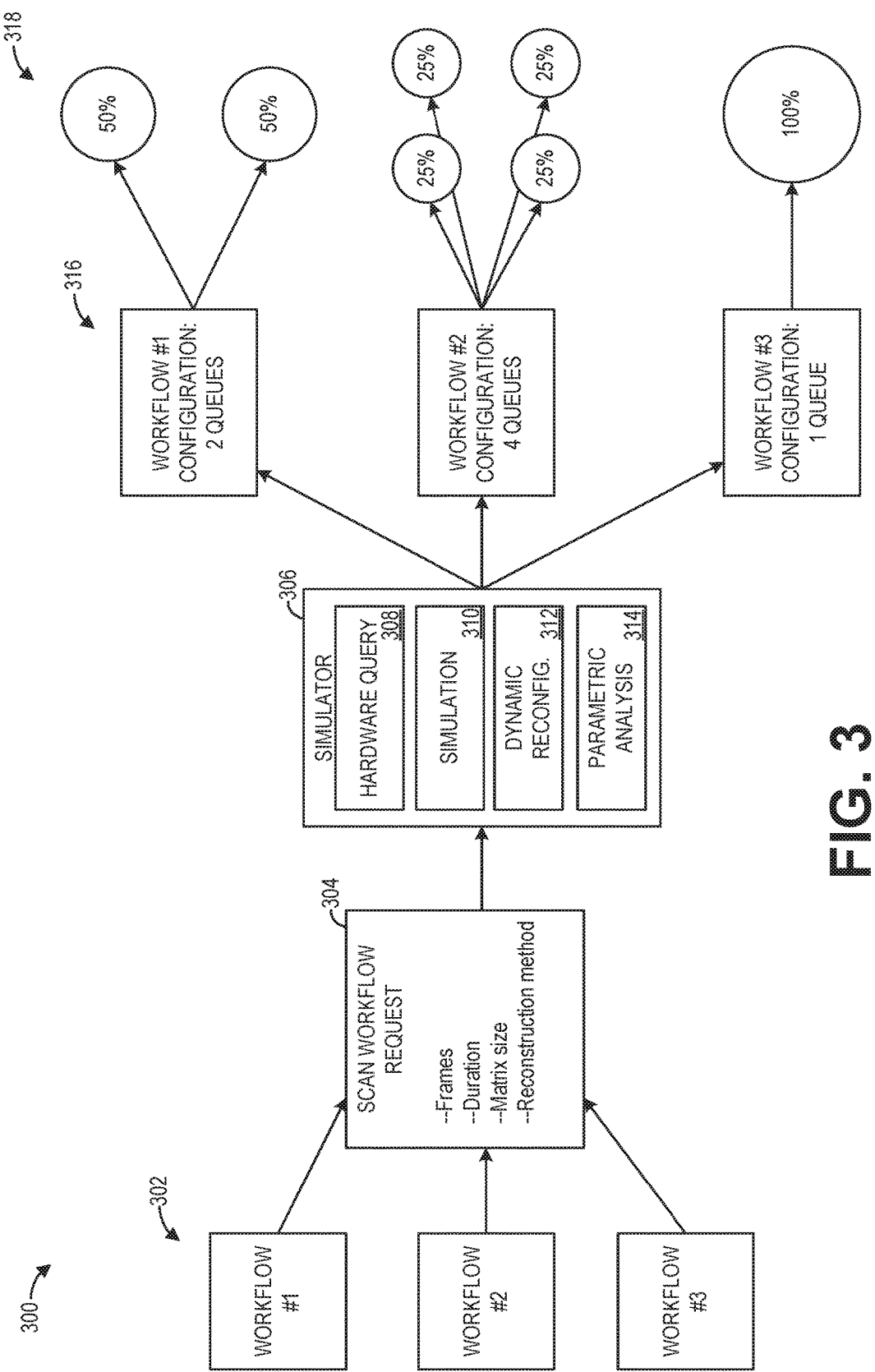
FIG. 3 is a block diagram illustrating an image reconstruction hardware allocation process according to an embodiment of the invention.

FIG. 3 shows a block diagram 300 illustrating an example image reconstruction hardware allocation process according to the disclosure. The image reconstruction hardware allocation process illustrated in FIG. 3 may be performed using a suitable computing device or devices, such as devices including the reconstruction processor 50 of FIG. 2, operably coupled to a medical imaging device, such as the PET scanner 14 of FIG. 2.

The image reconstruction hardware allocation process may include the reception, at the reconstruction processor, of a workflow request 304. In one example, the workflow request 304 may be identified from user input, where a user of the medical imaging device selects a desired workflow from a plurality of workflows stored in memory of the workstation associated with the medical imaging device, for example. The workstation may then communicate the selected workflow to the reconstruction processor.

As shown in FIG. 3, the plurality of workflows may include workflow #1, workflow #2, and workflow #3. In one non-limiting example, workflow #1 may define a PET image reconstruction process for an oncology scanning session, workflow #2 may define a PET image reconstruction process for a cardiac scanning session, and workflow #3 may define a PET image reconstruction process for a research scanning session. Each workflow may specify target anatomy to be scanned and specific images (e.g., of various planes of the target anatomy) to be obtained during the scanning session. Each workflow also defines the image reconstruction parameters to be used during the image reconstruction process for reconstructing the images specified by the workflow. The image reconstruction parameters defined in the workflow may include the image reconstruction method (e.g., FBP, OSEM, MLEM), the number of scans during the scanning session, the number of frames/images, the duration of the scanning session, the matrix size of the data set generated during the scanning session, desired image resolution, desired number of iterations per image reconstruction job, number and/or types of desired corrections to be applied, and so forth. Each reconstruction parameter may be predefined by the workflow, or one or more reconstruction parameters may be user-defined at the time of the scanning session.

The image reconstruction parameters are communicated to a simulator 306. Simulator 306 is a non-limiting example of simulator 87 of FIG. 2. Simulator 306 identifies a target hardware resource allocation configuration for performing the image reconstruction process defined by the requested workflow, where the image reconstruction process includes one or more image reconstruction jobs. Each image reconstruction job results in reconstruction of an image from the medical imaging data received from the medical imaging device. To identify the target hardware resource allocation configuration, simulator 306 performs a hardware query using hardware query module 308. Based on the available hardware resources as determined by the hardware query, each possible hardware resource allocation configuration may be identified. For example, a predetermined list of possible hardware resource allocation configurations may be stored in memory of the simulator. In some examples, the predetermined list may be adjusted by the simulator based on prior data of previous image reconstruction processes.

A simulation of the image reconstruction process may then be performed by a simulation module 310. As explained above with respect to FIG. 2, the simulation may identify a "time to final image" for the image reconstruction process using each possible hardware resource allocation configuration, based on the reconstruction parameters as defined in the workflow request. The hardware resource allocation configuration that results in the shortest time to final image may be selected as the target hardware resource allocation configuration. For example, the simulator may store in memory (or may retrieve from an operably coupled memory) the durations and parameters to use for simulating the reconstruction time of an individual reconstruction job on different hardware configurations. Example numbers/parameters may include "each iteration takes 10 seconds with two GPUs, and 17 seconds with one GPU" and "scale the time by a factor of 1.5 for a 192×192 matrix size, or by 2.5 for a 256×256 matrix size." Once the times for individual jobs on a configuration have been computed, the simulator may use that information along with the acquisition parameters to estimate what the entire reconstruction process would look like to determine the time to final image. The process would then be repeated for all hardware configurations to determine the most optimal configuration for that reconstruction process.

A dynamic reconfiguration module 312 may control/instruct the various hardware resources of the reconstruction processor to perform the image reconstruction process according to the target hardware resource allocation configuration. In other examples, the dynamic reconfiguration module may communicate the target hardware resource allocation configuration to a suitable processor/control unit so that the image reconstruction process may commence according to the target hardware resource allocation configuration.

Further, in some examples, a parametric analysis module 314 may be included in the simulator 306 to perform parametric or other suitable analysis in order to determine the time to final image and/or to update the information used by the simulator to arrive at the time to final image for the reconstruction process. In one example, the actual duration for each image reconstruction job that is performed may be identified and stored in memory along with the defined image reconstruction parameters. Once sufficient reconstructions have been performed for a given image reconstruction parameter, the parametric analysis may be performed in order to determine the mean duration (or other suitable duration) for the reconstruction job associated with the given image reconstruction parameter. The duration for the reconstruction job may be updated by performing a parametric analysis based on other reconstruction parameters.

As illustrated in FIG. 3, a plurality of hardware resource allocation configurations 316 may be determined by simulator 306, with a respective hardware resource allocation configuration being determined for each workflow. The hardware resources 318 may then be allocated to different reconstruction tasks and/or jobs in order to perform the image reconstruction process according to the determined hardware resource allocation configuration.

As shown in FIG. 3, workflow #1 configuration is determined based on the reconstruction parameters defined by workflow #1 and includes two processing queues. Each processing queue may then utilize 50% of the hardware resources to perform the processing for the image reconstruction jobs or tasks in that queue. The processing for each queue may be done in parallel, such that the image reconstruction tasks in each queue are processed at the same time. Workflow #2 configuration is determined based on the reconstruction parameters defined by workflow #2 and includes four processing queues. Each processing queue may then utilize 25% of the hardware resources to perform the processing for the image reconstruction jobs or tasks in that queue. The processing for each queue may be done in parallel, such that the image reconstruction tasks in each queue are processed at the same time. Workflow #3 configuration is determined based on the reconstruction parameters defined by workflow #3 and includes one processing queue. The processing queue may then utilize 100% of the hardware resources to perform the processing for the image reconstruction tasks in that queue. In some examples, hardware resources may not be divided evenly among the queues. For example, a configuration may include three queues, one which has 50% of the resources and two that have 25% each.

Figure 4:
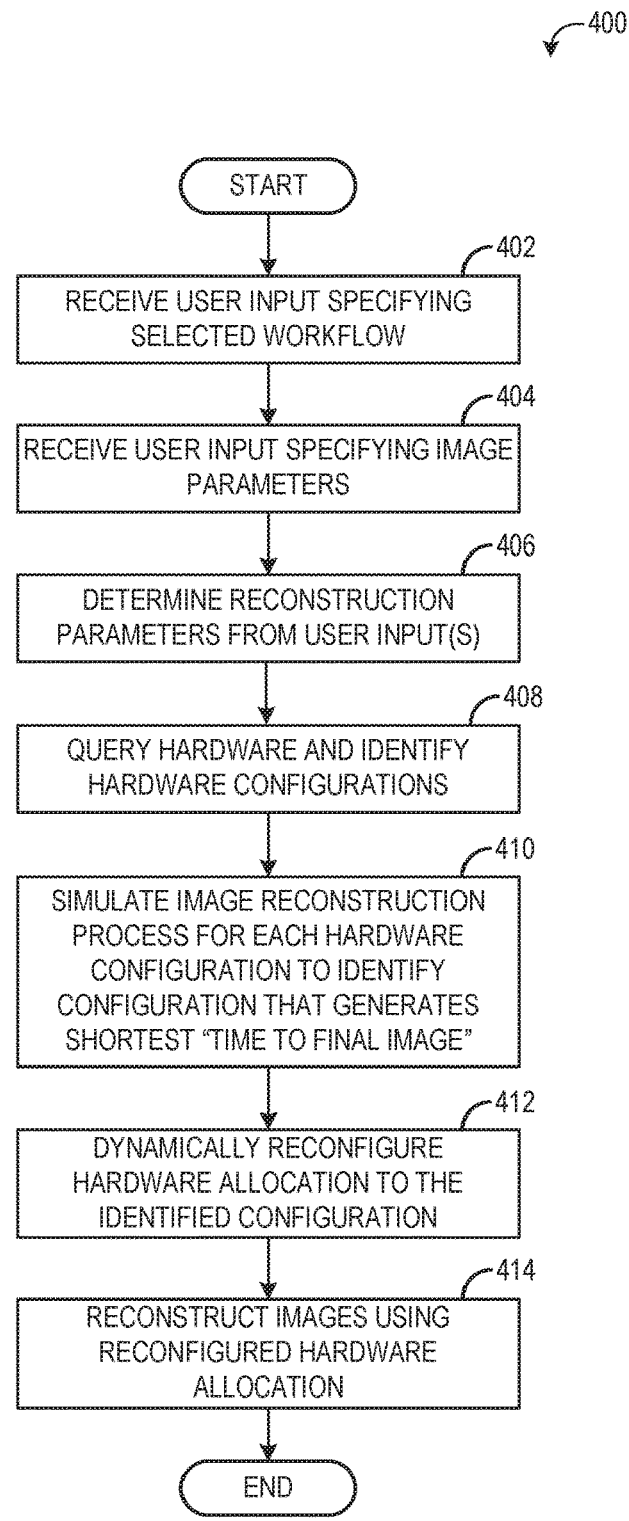
FIG. 4 is a flow chart illustrating a method for dynamic allocation of hardware resources during an image reconstruction process according to an embodiment of the invention.

Turning now to FIG. 4, an example method 400 for dynamically reconfiguring a hardware allocation configuration during an image reconstruction process is shown. Instructions for carrying out method 400 herein may be executed by a processor (e.g., reconstruction processor 50 of FIG. 2) based on instructions stored on a memory of the processor and in conjunction with medical imaging data received from a medical imaging device, such as the PET scanner of FIGS. 1-2.

At 402, method 400 includes receiving user input specifying a selected workflow. As explained above with respect to FIG. 3, a workflow may define parameters of a medical imaging scanning session, such as imaging modality (e.g., PET, CT, or both PET and CT), target anatomy or diagnostic goal (e.g., cardiac, oncology), number of images to be generated, position of a subject relative to the medical imaging device (e.g., table position), radiotracer dose, and so forth. The workflow may also define image reconstruction parameters, including but not limited to reconstruction method and data matrix size. In some examples, method 400 may include, at 404, receiving user input specifying image reconstruction parameters, such as image resolution, number of iterations, and the like. In other examples, such parameters may be defined by the workflow. At 406, method 400 includes determining reconstruction parameters from the user input(s). Thus, based on the selected workflow and optionally additional user selections, the image reconstruction parameters may be determined.

At 408, method 400 queries the hardware to determine available hardware resources and then identifies possible hardware configurations. At 410, method 400 simulates the image reconstruction process for each hardware configuration to identify the hardware configuration that generates the shortest "time to final image." As explained above with respect to FIGS. 2 and 3, the hardware resources of the reconstruction processor (which may include one or more CPUs, GPUs, FPGAs, and/or other integrated circuits) may be allocated into different queues. For example, all the resources may be combined into one queue. In another example, one CPU may form a first queue and one GPU may form another queue. In other examples, the image reconstruction tasks (e.g., individual reconstruction jobs or processing tasks that make up a reconstruction job) may be allocated into queues. At 412, method 400 dynamically reconfigures the hardware allocation to the identified configuration. As explained above, the hardware resources may be instructed to perform certain processing tasks in order to reconstruct the images, as specified by the selected hardware allocation configuration. At 414, method 400 reconstructs the images, from data received from the medical imaging device, according to the reconfigured hardware allocation. The images may be reconstructed using the specified reconstruction method, with the number of iterations as specified by the reconstruction parameters. Further, prior to, during, and/or after reconstruction, one or more corrections may be applied to reduce noise or artifacts. The reconstructed images may be displayed to a user via a display device communicatively coupled to the reconstruction processor (e.g., display 96 of FIG. 2) and/or saved in memory (e.g., of a PACS or RIS). Method 400 then returns.

Thus, method 400 described above provides for the reconstruction of a plurality of images using an optimal allocation of hardware resources in order to perform the reconstruction process in the shortest amount of time possible with the available resources. The method leverages supplemental information obtained from a medical imaging workflow (e.g., number of iterations to be performed, reconstruction method, matrix size) to automatically reallocate/redistribute hardware among the submitted image reconstruction jobs. In doing so, the hardware is allocated into processing queues dynamically, taking into account information about the workflow to provide an optimal image reconstruction setup. The method takes into account information about the acquisition protocol for the exam (number of frames/bed positions, acquisition duration, etc.), and the prescribed image reconstructions (e.g. matrix size, reconstruction method, corrections used). The method then may use pre-existing information to simulate the distribution of hardware that would result in the shortest time to final image, and set up that configuration. In this way, the amount of time for a batch of images to be reconstructed may be reduced (e.g., by 25%) relative to a standard, fixed hardware allocation, thus reducing the processing time and operating the reconstruction processor more efficiently.

While the examples have been presented herein with regard to PET imaging, it is to be understood that the examples may be used with other imaging modalities, such as MRI, without departing from the scope of this disclosure. It is to be understood that some reconstruction parameters may differ among different imaging modalities. For example, MRI data may be reconstructed using different reconstruction methods than PET data. Further, MRI data may be in a different format and/or of different size than PET data. Thus, the optimal hardware allocation configurations may differ for different imaging modalities. Further still, the examples presented herein may be used with multiple imaging modalities, such as CT-PET. In such examples, the reconstruction durations described above may be based on the reconstruction parameters for both modalities.

A technical effect of dynamically allocating hardware is reduced image reconstruction time for a plurality of images and increased device efficiency.

An example provides a method including receiving one or more image reconstruction parameters defining an image reconstruction process for reconstructing one or more images from medical imaging data; identifying a target hardware allocation based on the one or more image reconstruction parameters; and reconstructing, via computing device hardware as specified by the target hardware allocation, one or more images from the medical imaging data according to the image reconstruction process. Additionally or alternatively, identifying the target hardware allocation may include selecting a target hardware allocation, from among a plurality of possible hardware allocations, that results in a shortest image reconstruction process duration. Additionally or alternatively, the one or more image reconstruction parameters may include one or more of a number of images to be reconstructed, a selected image reconstruction method, a selected number of reconstruction iterations, and a number and/or type of corrections to be performed during the image reconstruction process. Additionally or alternatively receiving one or more image reconstruction parameters may include receiving user input defining the one or more image reconstruction parameters. Additionally or alternatively, receiving one or more image reconstruction parameters may include receiving a medical imaging workflow defining the one or more image reconstruction parameters. Additionally or alternatively, identifying the target hardware allocation may include identifying a number of processing queues, each processing queue associated with one or more hardware resources of the computing device hardware. Additionally or alternatively, the one or more image reconstruction parameters define one or more processing tasks to be performed during the image reconstruction process, and the method may further include allocating the one or more processing tasks of the image reconstruction process into the identified processing queues.

An example provides a system including a medical imaging device; and a reconstruction processor. The reconstruction processor includes a plurality of hardware resources and stores instructions executable by the reconstruction processor to receive an array of medical imaging data from the medical imaging device; receive a selected medical imaging workflow defining one or more image reconstruction parameters of an image reconstruction process for reconstructing one or more images from the array of medical imaging data; identify a target hardware allocation based on the one or more image reconstruction parameters; and reconstruct, via the plurality of hardware resources as specified by the target hardware allocation, one or more images from the medical imaging data according to the image reconstruction process. Additionally or alternatively the one or more image reconstruction parameters define one or more processing tasks to be performed during the image reconstruction process, and the instructions may be further executable to: identify the target hardware allocation by identifying a number of processing queues based on the reconstruction parameters; and allocate the one or more processing tasks into the processing queues. Additionally or alternatively the selected medical imaging workflow is a first medical imaging workflow for performing a first diagnostic routine, the number of processing queues comprises one processing queue, and the instructions are further executable to reconstruct, via the plurality of hardware resources in the one processing queue, one or more images from the medical imaging data according to the image reconstruction process, by performing each processing task serially across the available hardware resources. Additionally or alternatively the selected medical imaging workflow is a second medical imaging workflow for performing a second diagnostic routine, the number of processing queues comprises two or more processing queues, and the instructions are further executable to reconstruct, via the plurality of hardware resources in the two or more processing queues, one or more images from the medical imaging data according to the image reconstruction process, by performing at least some processing tasks in parallel across the available hardware resources. Additionally or alternatively performing at least some processing tasks in parallel across all available hardware resources comprises performing a first processing task using a first subset of the available hardware resources and simultaneously performing a second processing task using a second subset of the available hardware resources. Additionally or alternatively, each processing task corresponds to a respective image reconstruction job, each image reconstruction job including instructions to reconstruct an image of the one or more images, the image reconstruction process comprising one or more image reconstruction jobs.

An example provides for a method including receiving one or more image reconstruction parameters defining an image reconstruction process for reconstructing one or more images from medical imaging data; identifying hardware resources of a computing device available for performing the image reconstruction process; based on the one or more image reconstruction parameters and the identified hardware resources, selecting a number of image processing queues; allocating each image reconstruction job of the image reconstruction process into a respective image processing queue; and reconstructing, via the hardware resources, one or more images from the medical imaging data according to the image reconstruction process via the selected number of processing queues. Additionally or alternatively, selecting the number of image processing queues may include selecting one processing queue; allocating each image reconstruction job of the image reconstruction process into a respective image processing queue may include allocating each image reconstruction job into the one processing queue; and reconstructing one or more images may include reconstructing each image serially using the hardware resources. Additionally or alternatively, selecting the number of image processing queues may include selecting at least two processing queues; allocating each image reconstruction job of the image reconstruction process into a respective image processing queue may include allocating a first image reconstruction job into a first image processing queue of the at least two image processing queues and a second image reconstruction job into a second image processing queue of the at least two image processing queue; and reconstructing one or more images may include reconstructing a first image according to the first image reconstruction job using a first subset of the hardware resources and reconstructing a second image according to the second image reconstruction job using a second subset of the hardware resources. Additionally or alternatively, the first image and the second image may be reconstructed simultaneously. Additionally or alternatively, selecting the number of image processing queues may include calculating, from information stored in memory of the computing device, an image reconstruction process duration for each possible number of image processing queues and selecting the number of image processing queues that provides the shortest image reconstruction process duration. Additionally or alternatively, the information may include a predicted duration for each image reconstruction job based on associated image reconstruction parameters. Additionally or alternatively, the method may further include updating the information based on a measured duration of each image reconstruction job during the reconstructing of the one or more images.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   receiving one or more image reconstruction parameters defining an image reconstruction process for reconstructing one or more images from medical imaging data;
   identifying a target hardware allocation based on the one or more image reconstruction parameters, including selecting the target hardware allocation, from among a plurality of possible hardware allocations, that results in a shortest image reconstruction process duration; and
   reconstructing, via computing device hardware as specified by the target hardware allocation, one or more images from the medical imaging data according to the image reconstruction process.

2. The method of claim 1, wherein the one or more image reconstruction parameters comprises one or more of a number of images to be reconstructed, a selected image reconstruction method, a selected number of reconstruction iterations, and a number and/or type of corrections to be performed during the image reconstruction process.

3. The method of claim 1, wherein receiving one or more image reconstruction parameters comprises receiving user input defining the one or more image reconstruction parameters.

4. The method of claim 1, wherein receiving one or more image reconstruction parameters comprises receiving a medical imaging workflow defining the one or more image reconstruction parameters.

5. The method of claim 1, wherein identifying the target hardware allocation further comprises identifying a number of processing queues, each processing queue associated with one or more hardware resources of the computing device hardware.

6. The method of claim 5, wherein the one or more image reconstruction parameters define one or more processing tasks to be performed during the image reconstruction process, and further comprising allocating the one or more processing tasks of the image reconstruction process into the identified processing queues.

7. A system, comprising:
   a medical imaging device; and
   a reconstruction processor comprising a plurality of hardware resources and storing instructions executable by the reconstruction processor to:
      receive an array of medical imaging data from the medical imaging device;
      receive a selected medical imaging workflow defining one or more image reconstruction parameters of an image reconstruction process for reconstructing one or more images from the array of medical imaging data, the one or more image reconstruction parameters defining one or more processing tasks to be performed during the image reconstruction process;
      identify a target hardware allocation based on the one or more image reconstruction parameters by identifying a number of processing queues based on the reconstruction parameters;
      allocate the one or more processing tasks into the processing queues; and
      reconstruct, via the plurality of hardware resources as specified by the target hardware allocation, one or more images from the medical imaging data according to the image reconstruction process.

8. The system of claim 7, wherein the selected medical imaging workflow is a first medical imaging workflow for performing a first diagnostic routine, wherein the number of processing queues comprises one processing queue, and wherein the instructions are further executable to reconstruct, via the plurality of hardware resources in the one processing queue, one or more images from the medical imaging data according to the image reconstruction process, by performing each processing task serially across the available hardware resources.

9. The system of claim 7, wherein the selected medical imaging workflow is a second medical imaging workflow for performing a second diagnostic routine, wherein the number of processing queues comprises two or more processing queues, and wherein the instructions are further executable to reconstruct, via the plurality of hardware resources in the two or more processing queues, one or more images from the medical imaging data according to the image reconstruction process, by performing at least some processing tasks in parallel across the available hardware resources.

10. The system of claim 9, wherein performing at least some processing tasks in parallel across all available hardware resources comprises performing a first processing task using a first subset of the available hardware resources and simultaneously performing a second processing task using a second subset of the available hardware resources.

11. The system of claim 7, wherein each processing task corresponds to a respective image reconstruction job, each image reconstruction job including instructions to reconstruct an image of the one or more images, the image reconstruction process comprising one or more image reconstruction jobs.

12. A method, comprising:
receiving one or more image reconstruction parameters defining an image reconstruction process for reconstructing one or more images from medical imaging data;
identifying hardware resources of a computing device available for performing the image reconstruction process;
based on the one or more image reconstruction parameters and the identified hardware resources, selecting a number of image processing queues;
allocating each image reconstruction job of the image reconstruction process into a respective image processing queue; and
reconstructing, via the hardware resources, one or more images from the medical imaging data according to the image reconstruction process via the selected number of processing queues.

13. The method of claim 12, wherein:
selecting the number of image processing queues comprises selecting one processing queue;
allocating each image reconstruction job of the image reconstruction process into the respective image processing queue comprises allocating each image reconstruction job into the one processing queue; and
reconstructing one or more images comprises reconstructing each image serially using the hardware resources.

14. The method of claim 12, wherein:
selecting the number of image processing queues comprises selecting at least two processing queues;
allocating each image reconstruction job of the image reconstruction process into the respective image processing queue comprises allocating a first image reconstruction job into a first image processing queue of the at least two image processing queues and a second image reconstruction job into a second image processing queue of the at least two image processing queue; and
reconstructing one or more images comprises reconstructing a first image according to the first image reconstruction job using a first subset of the hardware resources and reconstructing a second image according to the second image reconstruction job using a second subset of the hardware resources.

15. The method of claim 14, wherein the first image and the second image are reconstructed simultaneously.

16. The method of claim 12, wherein selecting the number of image processing queues comprises calculating, from information stored in memory of the computing device, an image reconstruction process duration for each possible number of image processing queues and selecting the number of image processing queues that provides the shortest image reconstruction process duration.

17. The method of claim 16, wherein the information comprises a predicted duration for each image reconstruction job based on associated image reconstruction parameters.

18. The method of claim 17, further comprising updating the information based on a measured duration of each image reconstruction job during the reconstructing of the one or more images.

* * * * *